(12) United States Patent
Brueck et al.

(10) Patent No.: US 9,804,073 B2
(45) Date of Patent: Oct. 31, 2017

(54) GAS SENSOR

(71) Applicant: Robert Bosch GmbH, Stuttgart (DE)

(72) Inventors: Marc Brueck, Bondorf (DE); Christopher Holzknecht, Stuttgart (DE); Martin Eckardt, Stuttgart (DE); Markus Linck-Lescanne, Wannweil (DE); Simon Rentschler, Stuttgart (DE); Karsten Storbeck, Heilbronn (DE); Thomas Brummel, Rutesheim (DE); Martin Schaaf, Stuttgart (DE); Christian Schuppler, Stuttgart-Zuffenhausen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 205 days.

(21) Appl. No.: 14/411,044

(22) PCT Filed: Jun. 6, 2013

(86) PCT No.: PCT/EP2013/061637
§ 371 (c)(1),
(2) Date: Dec. 23, 2014

(87) PCT Pub. No.: WO2014/001049
PCT Pub. Date: Jan. 3, 2014

(65) Prior Publication Data
US 2015/0192509 A1    Jul. 9, 2015

(30) Foreign Application Priority Data

Jun. 27, 2012   (DE) .................. 10 2012 211 039

(51) Int. Cl.
| | |
|---|---|
| *G01M 15/10* | (2006.01) |
| *G01N 15/06* | (2006.01) |
| *G01N 33/00* | (2006.01) |

(52) U.S. Cl.
CPC .......... *G01N 15/06* (2013.01); *G01M 15/102* (2013.01); *G01N 33/0009* (2013.01); *G01N 33/0011* (2013.01); *G01N 15/0656* (2013.01)

(58) Field of Classification Search
CPC . G01M 15/102; G01N 15/06; G01N 15/0656; G01N 33/0009; G01N 33/0011
See application file for complete search history.

(56) References Cited

U.S. PATENT DOCUMENTS

| | | | | |
|---|---|---|---|---|
| 4,624,770 A | * | 11/1986 | Yamada ............. | G01N 27/4077 204/425 |
| 6,346,179 B1 | * | 2/2002 | Makino .............. | G01N 27/4077 204/426 |

(Continued)

FOREIGN PATENT DOCUMENTS

| | | | | |
|---|---|---|---|---|
| DE | 102004033958 | | 2/2006 | |
| DE | 102006035058 | * | 1/2008 | ............... F01N 9/00 |

(Continued)

OTHER PUBLICATIONS

International Search Report for PCT/EP2013/061637, issued on Aug. 28, 2013.

*Primary Examiner* — Randy Gibson
*Assistant Examiner* — Gedeon M Kidanu
(74) *Attorney, Agent, or Firm* — Norton Rose Fulbright US LLP; Gerard Messina

(57) ABSTRACT

Gas sensors are provided that are fashioned such that there is an increased flow over the sensor element. In this way, a good measurement dynamic is achieved even when these gas sensors are exposed to exhaust gases having a low flow speed.

8 Claims, 3 Drawing Sheets

(56) References Cited

U.S. PATENT DOCUMENTS

| | | | | |
|---|---|---|---|---|
| 8,001,827 B2 * | 8/2011 | Weyl | ............... | G01N 27/4077 |
| | | | | 73/23.31 |
| 2008/0073209 A1 * | 3/2008 | Yamada | ............ | G01N 27/4071 |
| | | | | 204/424 |
| 2014/0305188 A1 * | 10/2014 | Kume | ............... | G01N 33/0009 |
| | | | | 73/23.2 |

FOREIGN PATENT DOCUMENTS

| | | | | |
|---|---|---|---|---|
| DE | 102008041038 | * | 2/2010 | ......... G01N 27/4074 |
| DE | 102008041046 | * | 2/2010 | ......... G01N 27/4077 |
| DE | WO 2015058873 A1 | * | 4/2015 | ......... G01N 27/4077 |
| WO | WO2005/017515 | | 2/2005 | |

* cited by examiner

GAS SENSOR

FIELD OF THE INVENTION

The present invention is based on a gas sensor for determining at least one state variable of a measurement gas, in particular the particle concentration in the exhaust gas of a burner or of an internal combustion engine, as known for example from German Published Patent Application No. 102008041038 A1.

BACKGROUND INFORMATION

The exhaust gas sensors shown there have, on their end exposed to the exhaust gas, an outer and an inner protective tube that surround a ceramic sensor element. The protective tubes are shaped so that a guide flow occurs in which the sensor element is protected on the one hand from the impact of liquid components of the exhaust gas, such as water drops, and on the other hand there takes place a flow over a measurement area of the sensor element, essentially in the longitudinal direction of the sensor.

Due to the long path of the exhaust gas inside the protective tubes, and due to the rather low interaction of the exhaust gas with the measurement area of the sensor element when flowing over it in the longitudinal direction, such exhaust gas sensors are provided in particular for installation in exhaust gas trains of internal combustion engines and burners in which there is a relatively high flow speed, and/or in applications in which the demands on the dynamics of the measurement devices are rather low.

On the other hand, however, there is a need for exhaust gas sensors that can also perform measurements with good dynamic behavior even in the exhaust gas trains of internal combustion engines and burners in which there is only a low flow speed. For example, such sensors, fashioned as soot sensors and installed in an exhaust gas box of a commercial vehicle, are intended to collect a minimum quantity of soot within a specified time period, so that a precise measurement of the quantity of soot emitted by the internal combustion engine of the commercial vehicle is possible.

SUMMARY

The gas sensors according to the present invention are therefore designed such that there is an increased flow past the sensor element. Even when these gas sensors are exposed to exhaust gases having low flow speed, in this way a good measurement dynamic is achieved.

The embodiment of the gas sensors according to the present invention can in principle take place according to one or more of three embodiments.

According to a first embodiment, according to the present invention one or more, for example two, gas inlets are provided that are situated on the jacket surface of the outer protective tube and are fashioned in particular as swirl valves. According to this embodiment, it can be provided in particular that the outer protective tube is closed at its end face, i.e. does not have any gas inlets.

According to a second embodiment, according to the present invention it is provided that the inner protective tube has one or more gas inlets in its jacket surface.

It can in particular be provided that the inner protective tube has only one gas inlet, and this gas inlet is made up of a single opening. The flow of the gas into the internal chamber of the inner protective tube, i.e. its flow to the sensor element, is then possible only via this one gas inlet. This can be realized in such a way that there is a directional flow onto the sensor element inside the inner protective tube. In this case, it is preferable that the gas sensor be fashioned as a soot sensor, and that the one gas inlet be oriented toward an interdigital electrode of the sensor element.

Exhaust gas sensors according to the second embodiment can have in particular an inner protective tube whose gas inlet or gas inlets are situated only downstream relative to the situation in the exhaust gas train of an internal combustion engine or of a burner. Alternatively or in addition, it can be provided that exhaust gas sensors according to the second embodiment have outer protective tubes that have one or more, for example two, gas inlets, and this gas inlet or inlets is/are fashioned in particular as swirl valves, these gas inlets being situated only upstream in particular relative to the situation in the exhaust gas train of an internal combustion engine or of a burner.

For the directional installation of the sensor in an exhaust gas train, corresponding means can always be provided, which can include for example markings, locking means, cap nuts, bayonet couplings, and/or similar devices.

According to a third embodiment, exhaust gas sensors are provided that have only a one-part protective tube, i.e. an inner protective tube, but no outer protective tube. It can in particular be provided that the inner protective tube has only one gas inlet, and this inlet is made up of a single opening. The flow of the gas into the interior of the inner protective tube, i.e. its flow to the sensor element, is then possible only via this one gas inlet. This can be realized in such a way that there is a directional flow onto the sensor element inside the inner protective tube. In this case, it is preferable that the gas sensor be realized as a soot sensor, and that the one gas inlet be oriented toward an interdigital electrode of the sensor element.

Exhaust gas sensors according to the third embodiment can in particular have an inner protective tube whose gas inlet or gas inlets are situated only upstream relative to the situation in the exhaust train of an internal combustion engine or of a burner. In addition or alternatively, the sensor element and/or the gas outlet hole can be eccentrically offset relative to a mid-axis of the inner protective tube, in particular relative to the situation in the exhaust tract of an internal combustion engine or of a burner in the downstream direction.

For the directional installation of the sensor in an exhaust gas train, corresponding means can always be provided, which can for example include markings, locking means, cap nuts, bayonet couplings, and/or similar devices.

Sensors according to the present invention having the first, the second, and/or the third embodiment can for example be installed in those devices within an exhaust gas train of a burner or of an internal combustion engine in which the flow cross-section is increased and/or the flow speed is reduced. Sensors according to the present invention having the first, the second, and the third embodiment can for example be installed in bypass lines of an exhaust gas train. For example, sensors according to the present invention can be installed in an exhaust gas box, in particular of a commercial vehicle.

DETAILED DESCRIPTION

Figure 1:
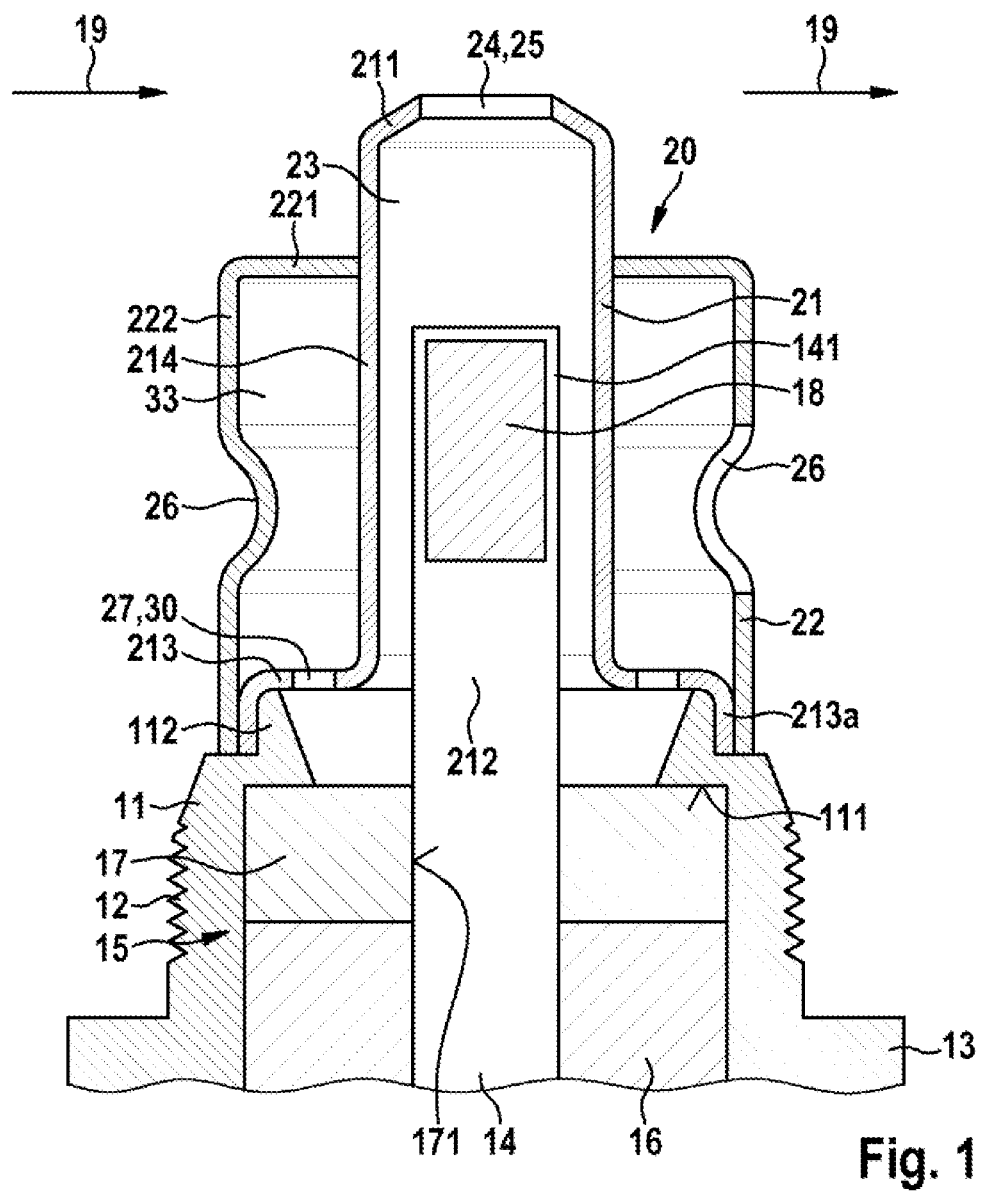
FIG. 1 shows an exhaust gas sensor according to the first embodiment of the present invention.

FIG. 1 shows a segment, oriented toward the exhaust gas, of a gas sensor according to the first embodiment of the present invention. This is a sensor for determining the particles, in particular the concentration of soot, in the exhaust gas of an internal combustion engine, also referred to as a particle sensor or soot sensor. It is indicated here as an example of a general gas sensor for determining at least one state variable of a measurement gas. Other gas sensors of this type include gas sensors for determining the oxygen concentration in the exhaust gas of an internal combustion engine, so-called lambda probes, or gas sensors for determining the nitrogen oxide concentration in the exhaust gas of an internal combustion engine. Temperature measurement probes for measuring the exhaust gas temperature can also be such a gas sensor.

The gas sensor shown in FIG. 1 has a metallic housing 11 that is provided for installation in a flow duct (not shown here) for the measurement gas, in particular in the exhaust gas tube of a burner or of an internal combustion engine, having a threaded segment 12 and a hexagonal key head 13. In housing 11, a sensor element 14 is installed in such a way that an end segment 141 protrudes from housing 11. The installation in housing 11 takes place using a sealing element 15 that in the exemplary embodiment is formed by a sealing packing made up of an elastic seal 16 pressed axially between two ceramic shaped parts, the seal pressing radially on sensor element 14 and on the inner wall of housing 11. In FIG. 1, only ceramic shaped part 17 situated on the end of housing 11 at the measurement gas side is shown; this shaped part has a central rectangular opening 171 for admitting sensor element 14 and is supported axially on a radial shoulder 111 formed in housing 11. On the gas-sensitive end segment 141 of sensor element 14, which for example has a rod-shaped ceramic body, on a large surface of the ceramic body there is situated a so-called interdigital electrode 18 for measuring a soot deposit brought about on end segment 141. Interdigital electrode 18 has two electrode segments that are fashioned in the manner of combs and whose comb teeth mesh together. The manner of functioning and the design of such an interdigital electrode for determining the quantity of soot deposited thereon as a measure for the concentration of soot in the exhaust gas is described in German Published Patent Application No. 10 2004 028 997 A1.

Gas-sensitive end segment 141 of sensor element 14 is covered by a protective tube module 20 that is provided with means for allowing the gas to pass through so that the measurement or exhaust gas flowing in the measurement gas flow channel, or in the exhaust gas pipe of the internal combustion engine, can reach gas-sensitive end segment 141. The direction of flow of the measurement or exhaust gas is indicated in FIG. 1 by flow arrows 19. Protective tube module 20 is made up of an inner protective tube 21 that is cap-shaped and that surrounds end segment 141 of sensor element 14 with a radial and axial spacing, and an outer protective tube 22 that is cap-shaped or pot-shaped and that surrounds the inner protective tube with a radial spacing. Cap-shaped inner protective tube 21 has a cap floor 211, a cap opening 212, and a cap brim 213 that surrounds cap opening 212. Cap floor 211 and cap brim 213 are connected via cap sheath 214, which is shaped as a cylindrical sheath. Outer edge 213a of cap brim 213 is bent off at a right angle, and grasps a fastening support 112 that is integrally formed in one piece on the end face of housing 11, the fastening support having an outer diameter that is reduced relative to the outer diameter of housing 11. Pot-shaped outer protective tube 22 has a pot floor 221 having a central circular opening 23 and a pot sheath 222 that is pushed over bent-off edge 213a of cap brim 213 of inner protective tube 21, so that an annular space 33 is present between inner protective tube 21 and outer protective tube 22 whose radial width matches the width of cap brim 213. The axial length of outer protective tube 22 is significantly smaller than the axial length of inner protective tube 21, so that the latter passes through circular opening 23 in the pot floor and extends significantly past pot floor 221. Protective tube module 20 is fastened with a material fit on fastening support 112 of housing 11, for example by a circumferential weld seam.

The means provided in protective tube module 20 for allowing the gas to pass through include a gas outlet 24 in inner protective tube 21 that is formed for example by a central hole 25 in cap floor 211 of inner protective tube 21, a gas inlet 26 in outer protective tube 22, and a gas inlet 27 in inner protective tube 21. Gas inlet 26 in outer protective tube 22 is realized by one or more openings formed in pot sheath 222, in particular as one or more holes and/or as one or more swirl valves. Gas inlet 27 in inner protective tube 21 is situated in cap brim 213, and in the direction of flow of the measurement gas flowing into protective tube module 20 behind cap brim 213, i.e. toward housing 11, there is provided an open space 29 extending underneath cap opening 212. Gas inlet 27 is realized with openings 30 in cap brim 213 that are situated at a distance from one another in the circumferential direction of cap brim 213. Preferably, openings 30 are fashioned as circular holes. In open space 29 there are situated flow means that divert the flow of measurement gas passing through openings 30 toward cap opening 212.

The openings or swirl valves formed in the pot sheath have the effect that even in the case of slow-flowing exhaust gas, exhaust gas can move with a high dynamic behavior into the interior of the sensor and to sensor element 14, even if a protection of sensor element 14 against the impact of liquid components of the exhaust gas, such as water droplets, is also present.

Figure 2:
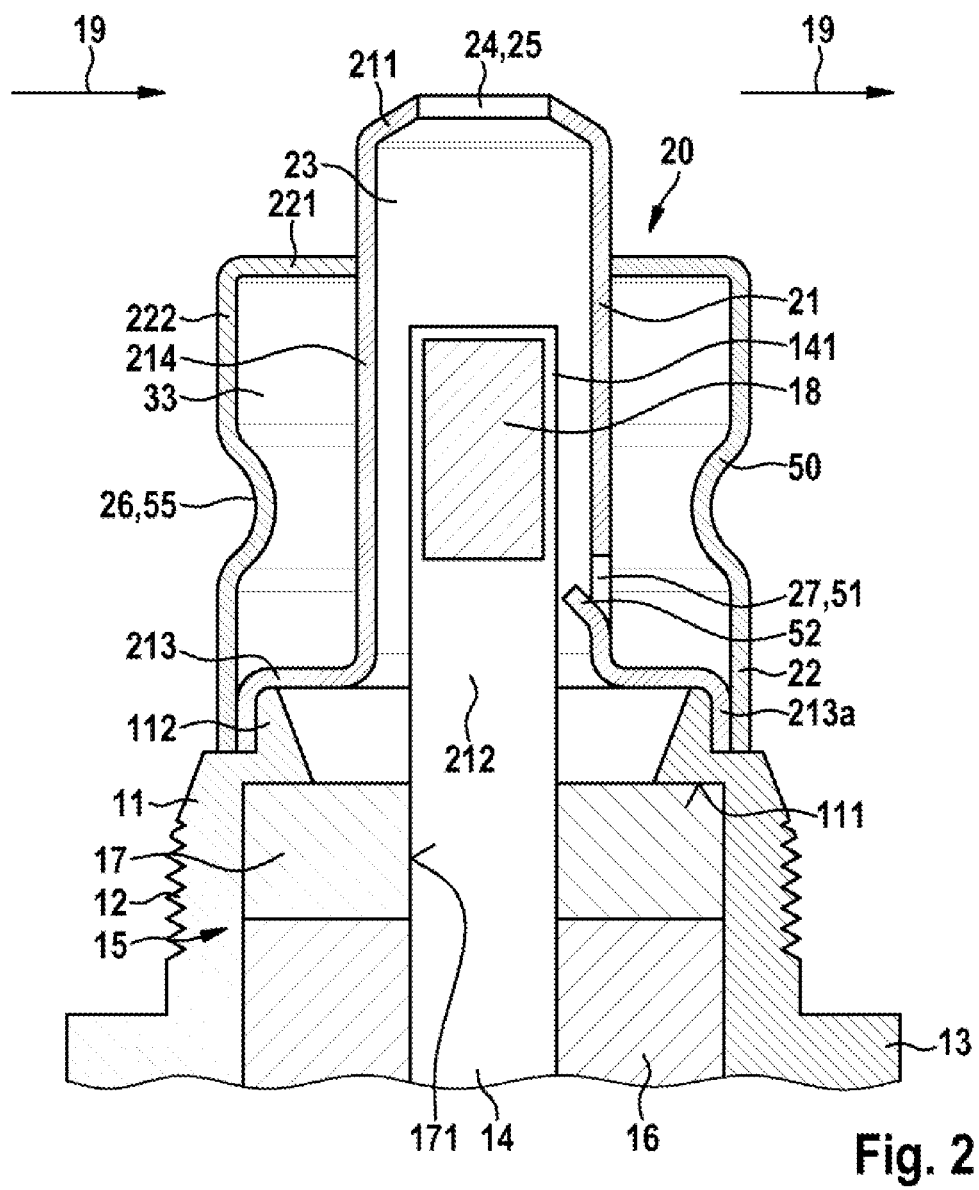
FIG. 2 shows an exhaust gas sensor according to the second embodiment of the present invention.

FIG. 2 shows a segment, oriented toward the exhaust gas, of a gas sensor according to the second embodiment of the present invention. This is a sensor for determining the particles, in particular the concentration of soot, in the exhaust gas of an internal combustion engine, also called a particle sensor or soot sensor. It is indicated here as an example of a general gas sensor for determining at least one state variable of a measurement gas. Other gas sensors of this type include gas sensors for determining the oxygen concentration in the exhaust gas of an internal combustion engine, so-called lambda probes, or gas sensors for determining the nitrogen oxide concentration in the exhaust gas of an internal combustion engine. Temperature measurement probes for measuring the exhaust gas temperature can also be such a gas sensor.

The gas sensor shown in FIG. 2 has a metallic housing 11 that is provided for installation in a flow duct (not shown here) for the measurement gas, in particular in the exhaust gas tube of a burner or of an internal combustion engine, having a threaded segment 12 and a hexagonal key head 13. In housing 11, a sensor element 14 is installed in such a way that an end segment 141 protrudes from housing 11. The installation in housing 11 takes place using a sealing element 15 that in the exemplary embodiment is formed by a sealing packing made up of an elastic seal 16 pressed axially between two ceramic shaped parts, the seal pressing radially on sensor element 14 and on the inner wall of housing 11. In FIG. 2, only ceramic shaped part 17 situated on the end of housing 11 at the measurement gas side is shown; this shaped part has a central rectangular opening 171 for admitting sensor element 14 and is supported axially on a radial shoulder 111 formed in housing 11. On the gas-sensitive end segment 141 of sensor element 14, which for example has a rod-shaped ceramic body, on a large surface of the ceramic body there is situated a so-called interdigital electrode 18 for measuring a soot deposit brought about on end segment 141. Interdigital electrode 18 has two electrode segments that are fashioned in the manner of combs and whose comb teeth mesh together. The manner of functioning and the design of such an interdigital electrode for determining the quantity of soot deposited thereon as a measure for the concentration of soot in the exhaust gas is described in German Published Patent Application No. 10 2004 028 997 A1.

Gas-sensitive end segment 141 of sensor element 14 is covered by a protective tube module 20 that is provided with means for the passage through of the gas so that the measurement or exhaust gas flowing in the measurement gas flow channel, or in the exhaust gas pipe of the internal combustion engine, can reach gas-sensitive end segment 141. The direction of flow of the measurement or exhaust gas is indicated in FIG. 1 by flow arrows 19. Protective tube module 20 is made up of an inner protective tube 21 that is cap-shaped and that surrounds end segment 141 of sensor element 14 with a radial and axial spacing, and an outer protective tube 22 that is cap-shaped or pot-shaped and that surrounds the inner protective tube with a radial spacing. Cap-shaped inner protective tube 21 has a cap floor 211, a cap opening 212, and a cap brim 213 that surrounds cap opening 212. Cap floor 211 and cap brim 213 are connected via cap sheath 214, which is shaped as a cylindrical sheath. Outer edge 213a of cap brim 213 is bent off at a right angle, and grasps a fastening support 112 that is integrally formed in one piece on the end face of housing 11, the fastening support having an outer diameter that is reduced relative to the outer diameter of housing 11. Pot-shaped outer protective tube 22 has a pot floor 221 having a central circular opening 23 and a pot sheath 222 that is pushed over bent-off edge 213a of cap brim 213 of inner protective tube 21, so that an annular space 33 is present between inner protective tube 21 and outer protective tube 22 whose radial width matches the width of cap brim 213. The axial length of outer protective tube 22 is significantly smaller than the axial length of inner protective tube 21, so that the latter passes through circular opening 23 in the pot floor and extends significantly past pot floor 221. Protective tube module 20 is fastened with a material fit on fastening support 112 of housing 11, for example by a circumferential weld seam.

The means provided in protective tube module 24 for admitting the gas include a gas outlet 24 in inner protective tube 21, formed for example by a central hole 25 in cap floor 211 of inner protective tube 21, a gas inlet 26 in outer protective tube 22, and a gas inlet 27 in inner protective tube 21. Gas inlet 26 in outer protective tube 22 is realized by one, two, or more than two openings formed in pot sheath 222, in particular as one, two, or more than two holes and/or as one, two, or more than two swirl valves 55. In particular, two swirl valves 55 can be provided that conduct a flow in directions that are tangentially opposite one another. Gas inlet 27 in inner protective tube 21 is placed in cap sheath 214, in particular in the half of the cap sheath facing away from the exhaust gas-side end of the gas sensor; this is at the bottom in FIG. 2. Gas inlet 27 in inner protective tube 21 is realized as a single opening 51 of cap sheath 214. Outer protective tube 22 can have, in the region of this single opening 51 of cap sheath 214, a bulge inward 50 so that the volume, or the width, of annular space 33 between protective tubes 21, 22 is reduced at this point.

Advantageously, at the edge of gas inlet 27, in cap sheath 214 there is provided an inwardly inclined flow-guiding element 52 that additionally diverts the flow of gas into the interior of inner protective tube 21.

It is in particular provided that gas inlet 27, in the present case the single opening 51 of cap sheath 214, and gas inlet 26 in outer protective tube 22 are fashioned on radially opposite sides of protective tube module 20, no gas inlet 26 being provided in outer protective tube 22 at the side of gas inlet 27, in the present case the single opening 51 of cap sheath 214.

It is in particular provided that gas inlet 27, in the present case the single opening 51 of cap sheath 214, and interdigital electrode 18 situated on the surface of sensor element 14 are situated such that they are oriented in the same radial direction.

Preferably, the sensor includes means for its directional installation, such as markings, locking means, cap nuts, bayonet couplings, and/or similar devices, so that gas inlet 27, in the present case the single opening 51 of cap sheath 214, can be installed at a downstream-situated side in an exhaust gas train.

Figure 3:
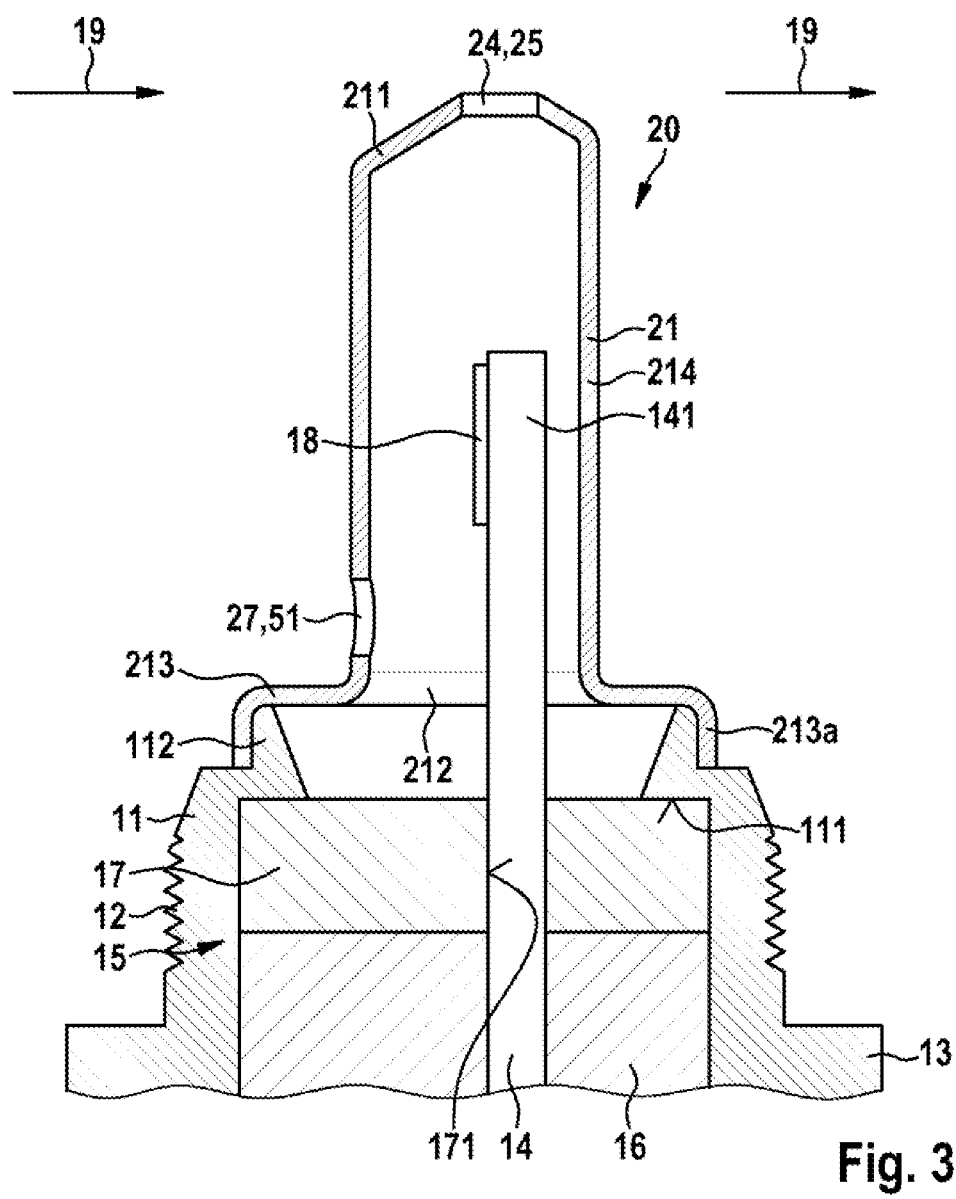
FIG. 3 shows an exhaust gas sensor according to the third embodiment of the present invention.

FIG. 3 shows a segment, oriented toward the exhaust gas, of a gas sensor according to the third embodiment of the present invention. This is a sensor for determining the particles, in particular the soot concentration, in the exhaust gas of an internal combustion engine, also called a particle sensor or soot sensor. It is indicated as an example of a general sensor for determining at least one state variable of a measurement gas. Other gas sensors of this type include gas sensors for determining the oxygen concentration in the exhaust gas of an internal combustion engine, so-called lambda probes, or gas sensors for determining the nitrogen oxide concentration in the exhaust gas of an internal combustion engine. Temperature measurement probes for measuring the exhaust gas temperature can also be such a gas sensor.

The gas sensor shown in FIG. 3 has a metallic housing 11 that is provided for installation in a flow duct (not shown here) for the measurement gas, in particular in the exhaust gas tube of a burner or of an internal combustion engine, having a threaded segment 13 and a hexagonal key head 13. In housing 11, a sensor element 14 is installed in such a way that an end segment 141 protrudes from housing 11. The installation in housing 11 takes place using a sealing element 15 that in the exemplary embodiment is formed by a sealing packing made up of an elastic seal 16 pressed axially between two ceramic shaped parts, the seal pressing radially on sensor element 14 and on the inner wall of housing 11. In FIG. 3, only ceramic shaped part 17 situated on the end of housing 11 at the measurement gas side is shown; this shaped part has a central rectangular opening 171 for admitting sensor element 14 and is supported axially on a radial shoulder 111 formed in housing 11. On gas-sensitive end segment 141 of sensor element 14, which for example has a rod-shaped ceramic body, on a large surface of the ceramic body there is situated a so-called interdigital electrode 18 for measuring a soot deposit brought about on end segment 141.

Interdigital electrode 18 has two electrode segments that are fashioned in the manner of combs and whose comb teeth mesh together. The manner of functioning and the design of such an interdigital electrode for determining the quantity of soot deposited thereon as a measure for the concentration of soot in the exhaust gas is described in German Published Patent Application No. 10 2004 028 997 A1.

Gas-sensitive end segment 141 of sensor element 14 is covered by a protective tube module 20 that is provided with means for the passage through of the gas so that the measurement or exhaust gas flowing in the measurement gas flow channel, or in the exhaust gas pipe of the internal combustion engine, can reach gas-sensitive end segment 141. The direction of flow of the measurement or exhaust gas is indicated in FIG. 1 by flow arrows 19. Protective tube module 20 is made up of an inner protective tube 21 that is cap-shaped and that surrounds end segment 141 of sensor element 14 with a radial and axial spacing. A further, outer, protective tube that surrounds the inner protective tube is not provided. Cap-shaped inner protective tube 21 has a cap floor 211, a cap opening 212, and a cap brim 213 that surrounds cap opening 212. Cap floor 211 and cap brim 213 are connected via cap sheath 214, which is shaped as a cylindrical sheath. Outer edge 213a of cap brim 213 is bent off at a right angle, and grasps a fastening support 112 that is integrally formed in one piece on the end face of housing 11, the fastening support having an outer diameter that is reduced relative to the outer diameter of housing 11.

The means provided in protective tube module 20 for admitting the gas include a gas outlet 24 in inner protective tube 21 that is formed for example by a hole 25 in cap floor 211 of inner protective tube 21. Gas inlet 27 in inner protective tube 21 is placed in cap sheath 214 and is realized as a single opening 51 of cap sheath 214. It is situated in the half of cap sheath 214 oriented toward cap brim 213, preferably in the one-third or one-fourth of cap sheath 214 oriented toward cap brim 213; in FIG. 3 this is at the bottom.

It is provided in particular that gas inlet 27, in the present case the single opening 51 of cap sheath 214, is fashioned on a radial side of protective tube module 20, while sensor element 14 is situated toward the opposite side, radially eccentrically, in housing 11 and/or in protective tube module 20.

It is in particular provided that gas inlet 27, in the present case the single opening 51 of cap sheath 214, is fashioned on a radial side of protective tube module 20, while gas outlet opening 24 is fashioned, radially eccentrically, as hole 25 in cap floor 211, oriented toward the opposite side. In particular, radially eccentrically situated sensor element 14 and radially eccentrically situated gas outlet opening 24 are situated one over the other, in a radial top view.

It is in particular provided that gas inlet 27, in the present case single opening 51 of cap sheath 214, and interdigital electrode 18, which is situated on the surface of sensor element 14, are configured in such a way that they are oriented in the same radial direction.

Preferably, the sensor includes means for its directional installation, such as markings, locking means, cap nuts, bayonet couplings, and/or similar devices, so that gas inlet 27, in the present case the single opening 51 of cap sheath 214, can be installed at the downstream side.

What is claimed is:

1. A gas sensor for determining at least one state variable of a measurement gas, comprising:
   a housing;
   a sensor element installed in the housing and including a gas-sensitive end segment that protrudes from the housing and is exposed to a flow of measurement gas;
   a protective tube module that covers the end segment and is fastened on the housing;
   an inner protective tube that is cap-shaped and that surrounds the end segment with a radial and axial spacing, the inner protective tube including a cap floor, a cap opening, and a cap brim;
   a pot-shaped outer protective tube that surrounds the inner protective tube with a radial spacing, the outer protective tube including a pot floor and a pot sheath that are set back relative to the cap floor, and the outer protective tube including an inward bulge to reduce a volume between the inner protective tube and the outer protective tube at a location of the inward bulge; and
   an arrangement, disposed in the protective tube module, for allowing the measurement gas to pass through, the arrangement having a gas outlet present in the cap floor of the inner protective tube and gas inlets present in the outer protective tube and in the inner protective tube, at least one gas inlet in the inner protective tube being placed in the cap brim, and an open space being present, in a direction of flow of the measurement gas behind the cap brim, that extends under the cap opening in order to divert the measurement gas flow into the inner protective tube, wherein the gas inlet present in the outer protective tube is situated in the inward bulge of the outer protective tube.

2. The gas sensor as recited in claim 1, wherein the state variable includes a particle concentration in an exhaust gas of one of an internal combustion engine and a burner.

3. The gas sensor as recited in claim 1, wherein the gas inlet is a swirl valve.

4. The gas sensor as recited in claim 1, wherein the outer protective tube has a pot floor not having a gas inlet.

5. A gas sensor for determining at least one state variable of a measurement gas, comprising:
   a housing;
   a sensor element installed in the housing and having a gas-sensitive end segment that protrudes from the housing and is exposed to a measurement gas flow;
   a protective tube module that covers the end segment and is fastened on the housing, the module having a cap-shaped inner protective tube that surrounds the end segment with a radial and axial spacing, the inner protective tube having a cap floor and cap sheath;
   a pot-shaped outer protective tube that surrounds the inner protective tube with a radial spacing, the outer protective tube having a pot floor and a pot sheath that are set back relative to the cap floor, and the outer protective tube including an inward bulge to reduce a volume between the inner protective tube and the outer protective tube at a location of the inward bulge; and
   an arrangement, provided in the protective tube module for the passage through of measurement the gas, the arrangement having a gas outlet present in the cap floor of the inner protective tube and gas inlets present in the inner protective tube and in the outer protective tube, wherein the gas inlet in the inner protective tube is fashioned in the cap sheath, and wherein the gas inlet present in the outer protective tube is situated in the inward bulge of the outer protective tube.

6. The gas sensor as recited in claim 5, wherein the state variable includes a particle concentration in an exhaust gas of one of an internal combustion engine and a burner.

7. The gas sensor as recited in claim 5, wherein a gas inlet is fashioned only on a radial side of the cap sheath of the inner protective tube.

8. The gas sensor as recited in claim 5, wherein a cap brim of the inner protective tube is fashioned without a gas inlet opening.

* * * * *